United States Patent [19]

Adachi

[11] Patent Number: 5,164,750
[45] Date of Patent: Nov. 17, 1992

[54] ASPHERIC SURFACE TOPOGRAPHER

[76] Inventor: Yoshi Adachi, 16241 Watson Cir., Westminster, Calif. 92683

[21] Appl. No.: 624,144

[22] Filed: Nov. 8, 1990

[51] Int. Cl.⁵ .............................. A61B 3/10
[52] U.S. Cl. ...................... 351/212; 351/247
[58] Field of Search .............. 351/212, 247; 356/124, 356/376, 359, 360

[56] References Cited

U.S. PATENT DOCUMENTS 4,692,003 9/1987 Adach et al. .................. 351/212

Primary Examiner—Rodney B. Bovernick
Attorney, Agent, or Firm—James T. English

[57] ABSTRACT

An instrument for measuring the surface contour of optical elements having aspheric surfaces accommodates large numerical aperture optical elements. A null lens composed of only spheric surfaces is inserted into the optical path for nulling an aspheric surface under test, such as parabola or hyperbola, so that the aberration is zero as indicated by a reduced Ronchi fringe image from a Ronchi test grating located at the optical path focus. The surface contour of the aspheric surface is obtained as equivalent to the conjugate of the null lens.

7 Claims, 2 Drawing Sheets

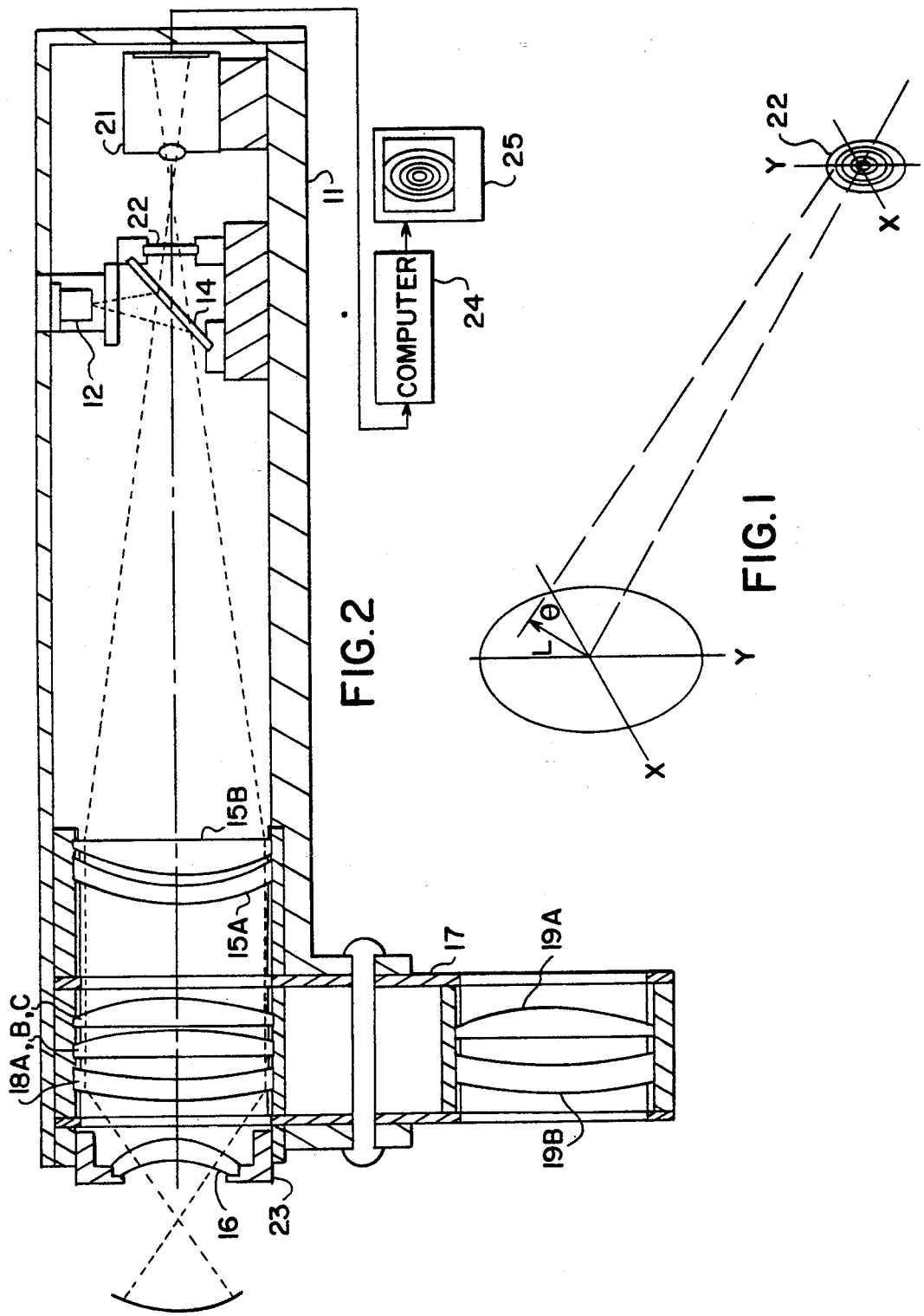

Ronchi Plot
K=0.1805
SII=0.0000
CII=0.0000
R20=0.7049
S22=0.0070
C22=0.0168
S31=-0.0071
C31=0.0005
S33=0.0052
C33=0.0014
R40=0.0459

K=1.8051
SII=0.0000
CII=0.0000
R20=1.0000
S22=0.0705
C22=0.1680
S31=-0.0706
C31=0.0054
S33=0.0525
C33=0.0144
R40=0.4589

ASPHERIC SURFACE TOPOGRAPHER

BACKGROUND OF THE INVENTION

This invention relates to optical instruments for determining the amount of curvature of a surface and includes all specular surfaces from spherical to aspherical. Prior art instruments were concerned with measurement of predominantly spherical objects such as the cornea of the eye, or shapes such as ball bearings. This invention is concerned with measurement of the curvature of surfaces such as parabolas and hyperbolas. Prior art instruments for measuring curvature cannot accommodate optical elements having large numerical apertures nor parabolic or hyperbolic surfaces.

BRIEF DESCRIPTION OF THE INVENTION

The present invention is a system for measuring the contour of any optical element having an aspherical specular surface such as hyperbolic or parabolic reflector surfaces, a cornea of an eye including the limbus or any aspherical mirror. In one embodiment of the invention a diode laser light source illuminates a target such as a cornea through a collimator lens, and a convergent lens, or a null lens in the case of an aspheric mirror. The wave front reflected from the surface is transmitted through a circular grating via a beam splitter and the Ronchi shadow fringes are imaged by a CCD camera. The camera image is frame-grabbed, digitized and analyzed by computer, and a topographical fringe map is then computed and displayed.

A Ronchi optical test method is used in which the camera sees the reflected wavefront fringes of the illumination wavefront modulated by the shape of an object placed in the illuminated area. In the Ronchi test method, the fringe pattern results from placing the circular grating slightly in front of the focus point of the reflected beam. The same number of fringes as there are rings in the circular grating are imaged by the camera. This reflected shadow fringe pattern from the target surface contains distortions due to surface irregularities of the target and is imaged and data processed to provide the topogram of the surface.

BRIEF DESCRIPTION OF THE DRAWINGS

FIG. 1 is a diagram illustrating the Notation used in the analysis method for the optical system.

FIG. 2 is a drawing of the optical elements to measure an aspherical surface.

DETAILED DESCRIPTION OF THE PREFERRED EMBODIMENTS

Figure 3:
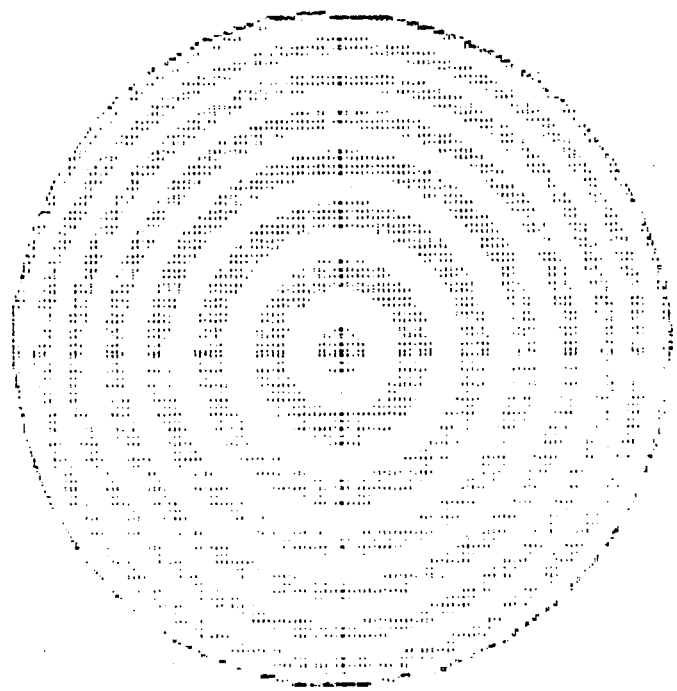
FIG. 3 is a Ronchi fringe pattern observed showing only the circular grating pattern with no target in the viewing area.

FIG. 1 is a diagram that shows the imaging area with respect to the shadow fringe polar coordinates. Any point in the imaging plane can be described by a vector of length L at angle $\theta$. This point has a corresponding polar coordinate on the circular grating shadow image due to the reticle 22. Computer processing of the polar coordinates of points on the wave front passing through reticle 22 provides Zernike coefficients from which the polynomial defining the wavefront can be generated and the fringe spacing computed. The processing will be described in detail following a description of the optical elements.

The optical structure is comprised of a point light source 12 which can be a diode laser, a collimating lens 15, elements A and B, whereby the beam is perfectly collimated, and a removable imaging lens 16. The beam is initially focused for measuring a near spherical concave or convex surface such as a cornea, without null lens 18A, B, C, with the turret 17 in a neutral (clear) position producing a near perfect circular fringe pattern used as a standard. For an aspherical surface, the lens 16 will be replaced by a calibrated null lens in the turret 17 which has an opposite spherical aberration to cancel the aberration of a target aspherical specular surface; therefore the combined spherical aberration of the null lens 18 and the specular surface under test is zero (null); the fringe pattern will then closely approximate the standard pattern.

For testing a target surface, the center of radius-of-curvature of the target is located at the focus of imaging lens 16. The return beam traces the same path as the propagation path and returns to near the point source 12. A beam splitter 14 is used to direct the return beam away from the light source so that a measuring device such as a grating 22 and CCD camera can be utilized. The circular grating 22 is placed in front of the image (i.e., the focus point) of the return beam. This arrangement of optical elements enables a Ronchi fringe test which produces the same number of fringes as there are rings in the circular grating. The shape of a target, spherical or aspherical, in the reflected illumination path, modulates the shape of the Ronchi fringes, indicating aberration of the target.

A CCD camera located behind the circular grating looks at the pupil of collimating lens 15. The shadow of circular grating 22 is seen by the camera 21; i.e., an image consisting of concentric fringes is observed. See FIG. 3. This image is modulated by the distortion of the target surface. If the target is a perfect sphere, there are equidistant concentric fringes. If the target is distorted to toric shape, there are elliptical shaped fringes. If the target is parabolic, the spacings of circular fringes become narrower towards the outside. See FIG. 4.

The pattern is digitized, analyzed using the mathematical methods to be described later and then the wave front; i.e., the surface topography is displayed.

The CCD camera 21 image is stopped; i.e., frame grabbed, and the frame is digitized under computer 24 program control. The digitized data contains the fringe image consisting of digital data distorted by the wavefront distortion. This frame of digital data is analyzed by the computer 24, and ring (Zernike) polynomials are developed having coefficients departing from the ring polynomials describing the circular grating rings. The polynomial coefficients describe the shape of the distorted rings in the fringe image displayed on the computer monitor 25.

Figure 4:
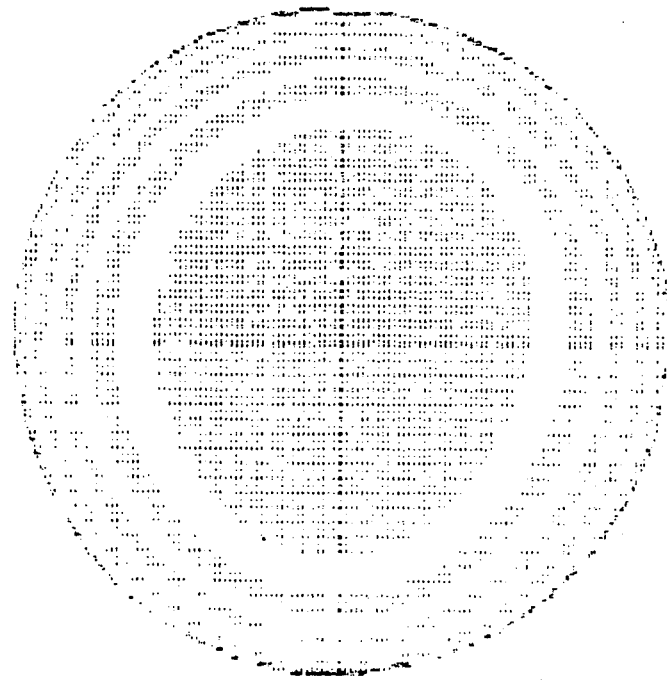
FIG. 4 is a Ronchi fringe pattern observed as a result of analysis of a target surface.

Thus, in FIGS. 3 and 4, there are differences of approximately 10 in the corresponding coefficients and a more edge-compressed image, FIG. 4, is obtained since the coefficients are larger.

It will be appreciated that this device is able to analyze large numerical aperture aspherical surfaces with high accuracy because the collimating lens 15 magnifies the combined wave front deformation of the imaging lens 16 and the target under test by the ratio of their focal lengths L1/L2 respectively.

For a near spherical target parabola, hyperbola or ellipse, a null lens such as 18A, B, C, can be an all spherical lens combination. For aspheric specular surfaces, having higher order than the 4th power, a zero order holographic grating in the form of a plurality of calibrated null lenses mounted in a turret, is located where the beam is perfectly collimated. These null lenses are substituted in the optical path to balance out aberrations until the standard fringe pattern is obtained. In practice, the calibrated null lenses such as 19A, B are inserted in sequence by means of the turret 17 to change the fringe pattern of FIG. 4 to that of FIG. 3. The null lens calibration is the measure of the aberration of the target article.

The circular grating Ronchi shadow fringe image is analyzed in polar coordinates by the method as follows:

The wave front $W(L,\theta)$ and the image coordinate $(x,y)$ are related by $$x = -F\left(\sin\theta \frac{dW}{dL} + \frac{\cos\theta}{L} \frac{dW}{d\theta}\right) \quad (1)$$

$$y = -F\left(\cos\theta \frac{dW}{dL} - \frac{\sin\theta}{L} \frac{dW}{d\theta}\right)$$

F is the distance from the surface to the beam converging point.

$$np = x \sin\theta + y \cos\theta \quad (2)$$
$$= -F\left(\frac{dW}{dL}\right)$$

$$W = K + S11 \sin\theta + C11 \cos\theta + R20 (2L - 1) + \quad (3)$$
$$S22\, L^2 \sin 2\theta + C22\, L^2 \cos 2\theta + S31 (3L^3 - 2L) \cos\theta +$$
$$R40 (6L^4 - 6L^2) + \ldots$$

$$dW/dL = K' + S11 \sin\theta + C11 \cos\theta + R20 (4L) + \quad (4)$$
$$R40 (24L^3 - 12L) + S22(2L) \sin 2\theta + C22 (2L) \cos 2\theta +$$
$$S31 (9L^2 - 2) \sin\theta + C31 (9L^2) \cos\theta + \ldots$$

The circular grating will be numbered from center to outside by n, where n is the integer. The $n^{th}$ circle coordinate will be np. Solving (2) and (4) we shall get Zernike coefficients S11, C11, R20, etc.

The coefficients thus obtained will be input to (3), which is the wave front and thus the surface contour is displayed.

NA is the numerical aperture.

Let Hm be the maximum height of optics, $$NA = \frac{Hm}{F} = \sin A.$$

Then fringe spacing $$Fs = \frac{1 - \cos A}{\tan A} np.$$

np is the numbers of fringes counted in the pupil of the optics under test. Fs may be called equivalent wave length. For wave length K, the factor Fs/K will be multiplied by Zernike coefficient. The result will be displayed in terms of wave length of K.

| | | | Zernike Radial polynomial Rmn | | | |
|---|---|---|---|---|---|---|
| n/m | 0 | 1 | 2 | 3 | 4 | 5 | 6 |
| 0 | 1 | | $2L^2-1$ | | $6L^4-6L^2+1$ | | $20L^6-30L^4+12L^2-1$ |
| 1 | | L | | $3L^3-2L$ | | $10L^5-12L^3+3L$ | |
| 2 | | | $L^2$ | | $4L^4-3L^2$ | | $15L^6-20L^4+6L^2$ |
| 3 | | | | $L^3$ | | $5L^5-4L^3$ | |
| 4 | | | | | $L^4$ | | $6L^6-5L^4$ |
| 5 | | | | | | $L^5$ | |
| 6 | | | | | | | $L^6$ |

Refer to Born & Wolf, "Principles of Optics", Mc Millan press, pg. 465, for higher order Zernike polynomials.

Another embodiment of the invention consists of an identical optical implementation except for a linear grating in lieu of the circular grating, with digitization in the x-y plane and computer processing to obtain the target surface modulated linear grating shadow pattern in x and y directions for mapping target aberration.

Hereinbefore have been described the preferred embodiments of the invention. It is recognized that other embodiments, modifications, and equivalents will readily occur to those skilled in the art and it is intended that the claims be interpreted as having all modifications and equivalents incorporated therein.

What is claimed is:

1. The method for realtime analysis of the shape of aspheric specular surfaces which comprises the steps of:
    illuminating an area for receiving said surface with electromagnetic spectrum wavelengths reflective to said surface, causing a beam wave front to be reflected from the area;
    focusing the reflected beam at a focal point;
    receiving the wave front in a transmission mode at a circular grating and camera, the circular grating placed in front of the focal point of the reflected beam, thereby developing a shadow fringe image of the circular grating in the camera;
    analyzing the flux intensity at points on the wave front in polar coordinates by computing the cross sectional intensity pattern of the wave front at the circular grating using a polynomial developed from the intensities at the polar coordinates to describe the wave front;
    placing the specular surface to be measured in the illuminated area;
    displaying the intensity pattern with the specular surface located in the illuminated area and observing the number of fringes;
    computing the distance between fringes at a plurality of points to determine the shape of the specular surface.

2. An instrument for topographical measurement of aspheric specular surfaces which comprises:

means for illuminating an area for receiving said specular surface, the area being reflective to said illuminating means;

a collimating lens receiving illumination from said illuminating means, for collimating the illumination;

an removeable imaging lens receiving and focusing light flux from said collimating lens onto a target specular surface to be measured;

means for successively inserting a plurality of calibrated null lenses in lieu of said imaging lens, said calibrated null lens receiving and focusing light flux from said collimating lens onto said specular surface;

means for receiving the reflected illumination wave front from said illuminated area;

a circular grating reticle receiving the reflected wave front from the area illuminated by said illuminating means, and transmitting said wavefront therethrough, imparting the image of said reticle rings on said wavefront;

means for detecting and converting the wave front having the image of said reticle, transmitted through said reticle, to electrical data having polar coordinates;

means for computing the differential illumination of the wave front reflected from the illuminated area through said reticle, from the wave front reflected from the target, through said reticle, receiving the electrical data from said means for detecting and converting, said computing means having an output;

means displaying the differential wave front output of said computing means;

whereby the topography of the aspheric specular surface is displayed.

3. An instrument for topographical measurement of aspheric specular surfaces as described in claim 2 wherein the aspheric specular surface is a cornea and limbus.

4. An instrument for topographical measurement of aspheric specular surfaces as described in claim 2 wherein the aspheric specular surface is the concave or the convex surface of a contact lens.

5. An instrument for topographical measurement of aspheric specular surfaces as described in claim 2 wherein the aspheric specular surface is the concave or convex surface of a mold for a plastic lens.

6. An instrument for topographical measurement of aspheric specular surfaces which comprises:

means for illuminating an area for receiving said specular surface, the area being reflective to said illuminating means;

a collimating lens receiving illumination from said illuminating means, for collimating the illumination;

an removeable imaging lens receiving and focusing light flux from said collimating lens onto a target specular surface to be measured;

means for successively inserting a plurality of calibrated null lenses in lieu of said imaging lens, said calibrated null lens receiving and focusing light flux from said collimating lens onto said specular surface;

means for receiving the reflected illumination wave front from said illuminated area;

a rectangular grating reticle receiving the reflected wave front from the area illuminated by said illuminating means, and transmitting the wavefront therethrough, imparting the image of said reticle on said wavefront;

means for detecting and converting the wave front having the image of said reticle, transmitted through said reticle, to electrical data having rectangular coordinates.

means for computing the differential illumination of the wave front reflected from the illuminated area through said reticle, from the wave front reflected from the target, through said reticle, receiving the electrical data from said means for detecting and converting, said computing means having an output;

means displaying the differential wave front output of said computing means;

whereby the topography of the aspheric specular surface is displayed.

7. The method for analysis of a beam wavefront in an optical system which comprises the steps of:

focusing the beam to a focus point;

inserting a circular grating before the focus point, and a camera after the focus point in the beam wavefront producing a shadow fringe image of the circular grating in the camera;

relating the wave front W and the image coordinates (x,y);

relating the period of the circular grating to the wavefront by $$np = -F\left(\frac{dW}{dL}\right);$$

relating the wavefront to polar coordinates $$\frac{dW}{dL};$$

developing the wavefront polynomial in polar coordinates;

determining Zernike coefficients and completing the wavefront polynomial;

developing the fringe spacing from the height of the optics and the numerical aperture;

displaying the fringe pattern;

whereby the fringe pattern displays the wavefront aberration of the optical system by the shape and spacing of the fringes.

* * * * *